United States Patent
Welters et al.

[11] Patent Number: 6,118,855
[45] Date of Patent: Sep. 12, 2000

[54] X-RAY EXAMINATION APPARATUS INCLUDING A FILTER

[75] Inventors: Wilhelmus J. J. Welters; Edward W. A. Young, both of Eindhoven, Netherlands

[73] Assignee: U.S. Philips Corporation, New York, N.Y.

[21] Appl. No.: 09/083,692

[22] Filed: May 21, 1998

[30] Foreign Application Priority Data

May 23, 1997 [EP] European Pat. Off. .............. 97201544

[51] Int. Cl.[7] ..................................... G21K 3/00
[52] U.S. Cl. ........................ 378/158; 378/156; 378/157
[58] Field of Search .................. 378/156, 157, 378/158

[56] References Cited

U.S. PATENT DOCUMENTS

| | | | |
|---|---|---|---|
| 4,125,776 | 11/1978 | Tosswill et al. | 378/149 |
| 5,270,549 | 12/1993 | Engdahl | 250/505.1 |
| 5,447,617 | 9/1995 | Shieh | 204/299 R |
| 5,559,853 | 9/1996 | Linders et al. | 378/159 |
| 5,625,665 | 4/1997 | Fokkink et al. | 378/156 |
| 5,666,396 | 9/1997 | Linders et al. | 378/156 |
| 5,751,786 | 5/1998 | Welters et al. | 378/156 |
| 5,768,340 | 6/1998 | Geittner et al. | 378/159 |
| 5,878,111 | 3/1999 | Schulz | 378/158 |
| 5,919,576 | 7/1999 | Hui et al. | 428/545 |
| 5,966,425 | 10/1999 | Marra et al. | 378/159 |

FOREIGN PATENT DOCUMENTS

WO96/13040  5/1996  European Pat. Off. ......... G21K 3/00

OTHER PUBLICATIONS

Plant et al, Biophysical Journal 67, 1126 (1994), Jun. 8, 1994.

*Primary Examiner*—David P. Porta
*Assistant Examiner*—Allen C. Ho
*Attorney, Agent, or Firm*—Dwight Renfrew

[57] ABSTRACT

X-ray examination apparatus including a filter An X-ray examination apparatus (1) includes an X-ray source (2), an X-ray detector (5) and an X-ray filter (6). The X-ray filter (6) is arranged between the X-ray source and the X-ray detector. The X-ray filter (6) includes a plurality of filter elements (7) whose X-ray absorptivity can be adjusted by adjusting a quantity of X-ray absorbing liquid (30) present in individual filter elements (7). The filter elements are formed by substantially parallel plates (8), respective plates being provided with separating members (10) which project approximately transversely from the plane of such a plate. The filter elements are formed notably by parallel corrugated plates or by parallel plates provided with partitions extending transversely from the plates.

22 Claims, 3 Drawing Sheets

X-RAY EXAMINATION APPARATUS INCLUDING A FILTER

BACKGROUND OF THE INVENTION

1. Field of the Invention

The invention relates to an X-ray examination apparatus which includes an X-ray source, an X-ray detector and an X-ray filter which is arranged between the X-ray source and the X-ray detector and comprises a plurality of filter elements whose X-ray absorptivity can be adjusted by controlling a quantity of an X-ray absorbing liquid in individual filter elements.

2. Description of the Related Art

An X-ray examination apparatus of this kind is known from the international patent application WO 96/13040.

The X-ray examination apparatus forms an X-ray image of an object to be examined, for example a patient to be radiologically examined. The X-ray source irradiates the object by means of an X-ray beam and an X-ray image is formed on the X-ray detector due to local differences in X-ray absorption within the object. The X-ray filter ensures that the range of brightness values of the X-ray image remains limited. The X-ray filter is adjusted so that on the one hand parts of the X-ray beam which are only slightly attenuated by the object are slightly attenuated by the X-ray filter and that, on the other hand, parts of the X-ray beam which are substantially attenuated by the object are transmitted by the X-ray filter substantially without attenuation. Because the brightness values of the X-ray image lie in a limited range, further processing of the X-ray image so as to achieve a clear reproduction of small details of low contrast, is very well possible.

The X-ray filter of the known X-ray examination apparatus comprises a very large number of glass capillary tubes, one end of each of which communicates with the X-ray absorbing liquid. The adhesion of the X-ray absorbing liquid to the inner wall of such a capillary tube is dependent on the electric voltage applied to the relevant capillary tube. Notably the contact angle enclosed by the X-ray absorbing liquid relative to the inner wall of such a capillary tube is dependent on the electric voltage difference between the inner wall and the X-ray absorbing liquid. When the contact angle is larger than 90°, the X-ray absorbing liquid hardly enters such a capillary tube; when the contact angle is less than 90°, such a capillary tube is filled with a quantity of X-ray absorbing liquid which is dependent on the magnitude of the electric potential difference. The quantity of X-ray absorbing liquid in each of the capillary tubes is controlled on the basis of the electric voltages applied to the capillary tubes.

The manufacture of the X-ray filter of the known X-ray examination apparatus is an intricate and hence expensive operation, because it is difficult to bundle a very large number of capillary tubes in a regular pattern.

SUMMARY OF THE INVENTION

It is an object of the invention to provide an X-ray examination apparatus having an X-ray filter which can be more simply manufactured.

This object is achieved by means of an X-ray examination apparatus according to the invention which is characterized in that the filter elements are formed by spaces between substantially parallel plates, respective plates being provided with separating members which project approximately transversely from the plane of such a plate.

The separating members bound the filter elements parallel to the plane of the plates, transversely of the plane of the plates, parts of the plates between neighboring separating members bound the filter elements. Pairs of adjacently situated plates automatically form filter elements which are always situated in a row parallel to the plates. Regular distances between the separating members on the plates provide a regular recurrence of filter elements in a row; regular distances between parallel plates provide a regular recurrence of rows of filter elements. The manufacture of such a construction is simple and hence inexpensive and the filter elements are arranged in a regular pattern with narrow tolerances. Preferably, the distances between the separating members on such a plate and the spacing of adjacently situated plates are chosen so that the filter elements constitute capillary tubes. One end of the filter elements communicates with an X-ray absorbing liquid. The quantity of X-ray absorbing liquid in the filter elements can be controlled, notably by application of an electric voltage to the individual filter elements.

An embodiment of an X-ray examination apparatus according to the invention is characterized in that the filter elements are formed by substantially parallel corrugated plates.

A flat plate can readily be provided with corrugations. For example, the flat plates can be provided with corrugations by pressing in a mould or by injection moulding. The corrugated plates are, for example plates provided with smooth corrugations or acute folds. A plurality of corrugated plates are arranged adjacent one another in such a manner that spaces between concave sides of oppositely situated corrugations of respective plates constitute the filter elements. The convex sides of the corrugations constitute the separating members. The corrugated plates preferably constitute filter elements in the form of capillary tubes.

An embodiment of an X-ray examination apparatus according to the invention includes filter elements having an essentially hexagonal cross-section. In that case there is hardly any or even no wasted space between the hexagonal capillary tubes. Consequently, the X-ray absorption can be adjusted across substantially the entire cross-section of the X-ray filter by control of the quantity of X-ray absorbing liquid in the hexagonal capillary tubes. Because hardly any wasted space remains between the hexagonal capillary tubes, comparatively thick corrugated plates can be used to form the hexagonal capillary tubes. Plates of this kind have a thickness of, for example some tens of micrometers.

The parallel plates in an embodiment of an X-ray examination apparatus according to the invention are provided with partitions which project transversely from the plane of the plate. The partitions are separating members which bound filter elements, notably capillary tubes, in the direction along the plates. Parts of the plates which are situated between neighboring partitions bound filter elements in the direction transversely of the plates. Flat plates can be readily provided with regularly spaced partitions. Such plates with partitions can be easily manufactured by means of wet chemical or plasma etching or by powder blasting with glass or a synthetic material.

An embodiment of an X-ray examination apparatus according to the invention includes adjacently situated plates which are interconnected between neighboring filter elements. Because neighboring plates are interconnected between neighboring filter elements, the filter elements, for example capillary tubes, are suitably separated from one another so that the X-ray absorbing liquid cannot, or only hardly, leak from one capillary tube to the other. Therefore, the quantity of X-ray absorbing liquid in individual capillary tubes can be very readily controlled independently of one another. Neighboring plates can be interconnected between the capillary tubes by attaching the plates to one another between the capillary tubes, preferably near the separating members, for example by bonding or fusion. A rigid construction is thus obtained for the X-ray filter. In order to separate the individual capillary tubes from one another it is not necessary to glue the plates to one another; it suffices to make neighboring plates contact one another between neighboring capillary tubes.

In an embodiment of an X-ray examination apparatus according to the invention an electrically conductive layer is provided between the separating members. The electric voltage is applied to the electrically conductive layer in order to control the quantity of X-ray absorbing liquid in the relevant capillary tube. The conductive layer is preferably situated on the inner wall of the relevant capillary tube in the X-ray filter. Furthermore, respective conductive layers of neighboring capillary tubes are electrically insulated from one another by the separating members, so that the electric voltage applied to one capillary tube is independent of the electric voltage applied to another capillary tube.

Because a separate conductive layer is used, the material for the corrugated plates can in principle be chosen arbitrarily; it is notably not necessary to use a conductive material for the corrugated plates. The corrugated plates, or the plates with partitions, are preferably made of a plastic foil or a glass foil.

In an embodiment of an X-ray examination apparatus according to the invention an electrically conductive layer is provided on a concave side of the relevant corrugation. The electrically conductive layer on the concave side of the corrugation is situated on the inner wall of the capillary tube constituted by the relevant corrugation. Consequently, the electric field caused by the electric voltage applied to the conductive layer can suitably penetrate the X-ray absorbing liquid. This electric field influences the adhesion of the X-ray absorbing liquid to the inner wall.

In an embodiment of an X-ray examination apparatus according to the invention an electrically insulating layer is provided on the electrically conductive layer and possibly a hydrophobic coating layer is provided on the electrically conductive layer. The electrically insulating layer ensures that the electrical capacitance between the X-ray absorbing liquid and the electrically conductive layer is sufficiently low so as to enable a fast X-ray filter response. The electrically insulating layer is preferably impermeable to the X-ray absorbing liquid so that breakdowns between the electrically conductive layer and the X-ray absorbing liquid are counteracted. The electrically insulating layer, however, can be coated with an sealing layer so as to avoid breakdowns. A dielectric layer is preferably used as the electrically insulating layer.

The hydrophobic coating layer ensures that whenever no electric voltage is applied to the relevant electrically conductive layer, the contact angle enclosed by the X-ray absorbing liquid relative to the coating layer is substantially larger than 90°. Depending on the materials used for the X-ray absorbing liquid and the wall of the filter elements, notably in the form of capillary tubes, in that case there is either no electric potential difference between the electrically conductive parts and the X-ray absorbing liquid or a residual electric potential difference exists due to an electrically charged double layer between the wall of the filter element and the X-ray absorbing liquid. The applied electric voltage changes the electric potential difference between the electrically conductive part and the X-ray absorbing liquid. Application or variation of an electric voltage reduces the contact angle; in the case of an adequate electric voltage the contact angle is reduced to a value below 90°, the filter element then being at least partly filled with the X-ray absorbing liquid. By choosing a hydrophobic coating layer it is achieved that the capillary tubes which do not receive an electric voltage are not filled with the X-ray absorbing liquid. When an electric voltage is applied to the electrically conductive layer of such a filter element, the contact angle is reduced to a value of less than 90°, so that the hydrophoby is cancelled and the relevant capillary tube is filled with the X-ray absorbing liquid. If no electric voltage is applied to a filter element, the X-ray absorptivity of the relevant filter element is negligibly small. By choosing a hydrophobic coating layer it is achieved that hardly any or no unintended residual X-ray absorbing liquid remains in the capillary tubes when no electric voltage is applied to the electrically conductive parts or tracks. Consequently, it is not necessary to take separate steps so as to empty the X-ray filter in the vicinity of the relevant electrically conductive parts of tracks. Undesirable (background) X-ray absorption by the filter is thus readily counteracted.

The conductive layer, the electrically insulating layer and the hydrophobic coating layer can be readily provided on the corrugated plates before their assembly so as to form the capillary tubes. It is even possible to provide such layers on flat plates or foils and to corrugate the plates or foils subsequently. It is also possible to provide the hydrophobic and electrically insulating layers after assembly of the plates; this offers the advantage that distortion of these layers due to the corrugation operation is avoided.

BRIEF DESCRIPTION OF THE DRAWING

These and other aspects of the invention will be described in detail hereinafter on the basis of the following embodiments and with reference to the accompanying drawing; therein

DETAILED DESCRIPTION OF THE PREFERRED EMBODIMENT

Figure 1:
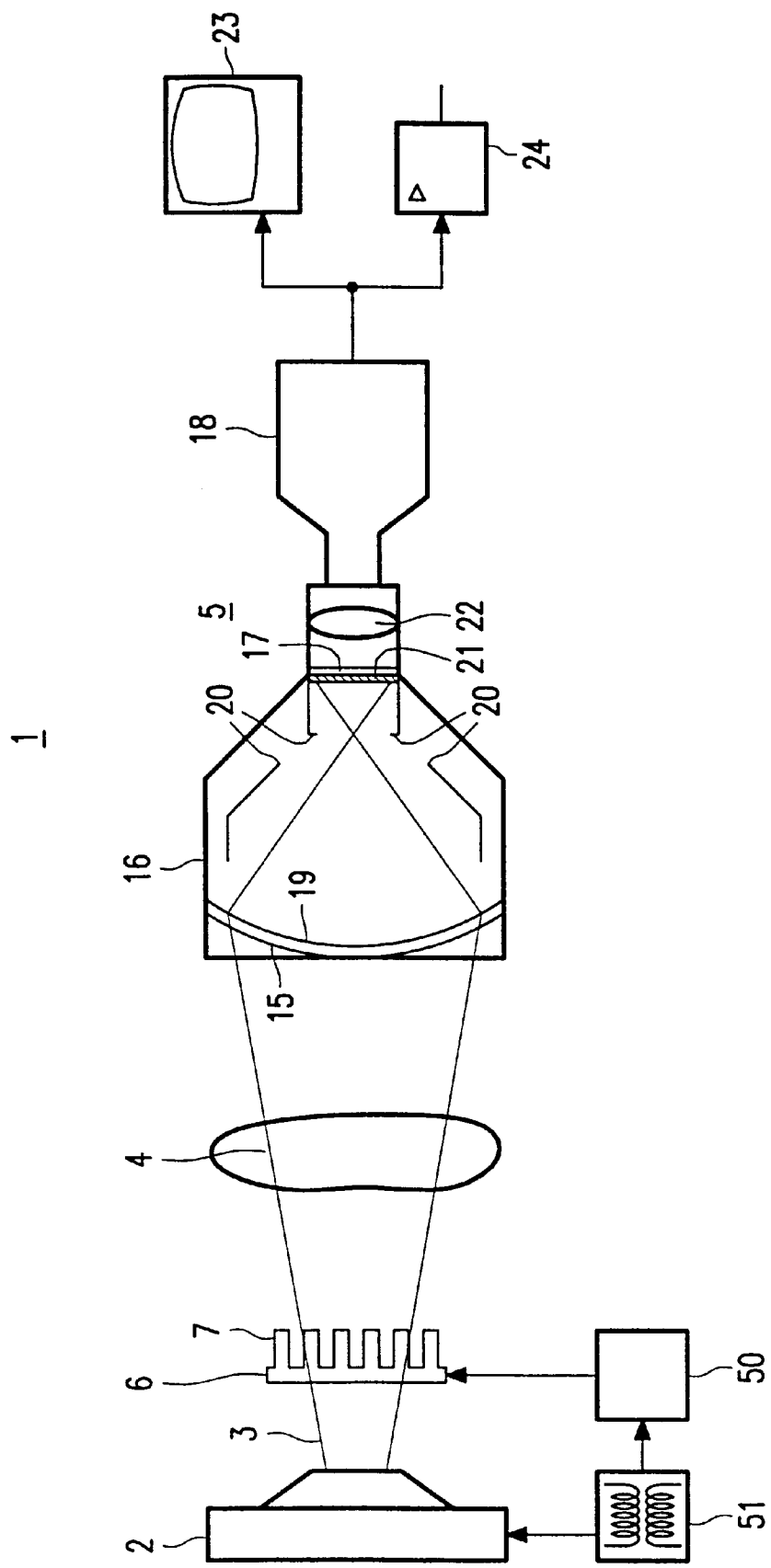
FIG. 1 shows diagrammatically an X-ray examination apparatus in which the invention is used.

FIG. 1 shows diagrammatically an X-ray examination apparatus 1 according to the invention. The X-ray source 2 emits an X-ray beam 3 for irradiating an object 4. Due to differences in X-ray absorption within the object 4, for example a patient to be radiologically examined, an X-ray image is formed on an X-ray-sensitive surface 15 of the X-ray detector 5 which is arranged opposite the X-ray source 2. A high-voltage power supply 51 applies an electric high voltage to the X-ray source 2. The X-ray detector 5 of the present embodiment is formed by an image intensifier pick-up chain which includes an X-ray image intensifier 16 for converting the X-ray image into an optical image on an exit window 17, and a video camera 18 for picking up the optical image. The entrance screen 19 acts as the X-ray-sensitive surface of the X-ray image intensifier which converts incident X-rays into an electron beam which is imaged on the exit window by means of an electron-optical system 20. The incident electrons form the optical image on a phosphor layer 21 of the exit window 17. The video camera 18 is coupled to the X-ray image intensifier 16 by means of an optical coupling 22, for example a lens system or an optical fiber coupling. The video camera 18 extracts an electronic image signal from the optical image, which image signal is applied to a monitor 23 in order to visualize the image information in the X-ray image. The electronic image signal can also be applied to an image processing unit 24 for further processing.

Between the X-ray source 2 and the object 4 there is arranged the X-ray filter 6 for local attenuation of the X-ray beam. The X-ray absorptivity of individual filter elements 7 of the X-ray filter 6 is adjusted by means of an adjusting unit 50. The adjusting unit 50 is coupled to the high-voltage power supply 51, thus enabling the X-ray filter 6 to be adjusted on the basis of the intensity of the X-ray beam 3 emitted by the X-ray source.

Figure 2:
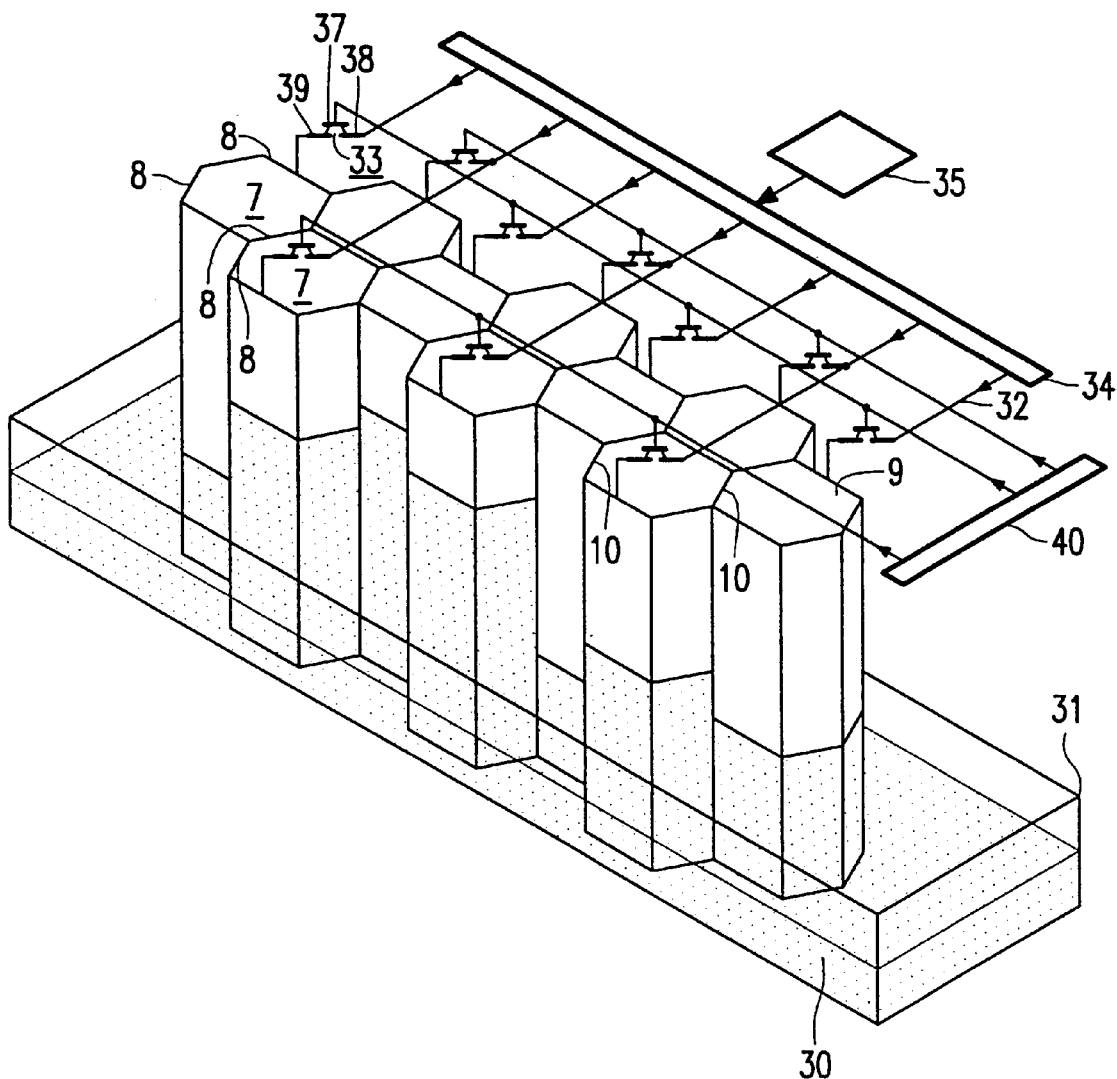
FIG. 2 shows diagrammatically an X-ray filter in which the invention is used.

FIG. 2 shows diagrammatically an X-ray filter of an X-ray examination apparatus according to the invention. The X-ray filter includes a number of substantially parallel corrugated plates 8 which constitute the filter elements 7. Neighboring corrugated plates are arranged in such a manner that concave sides of the corrugations of respective plates are always situated opposite one another. Opposite concave sides of respective plates constitute a capillary tube. For the simplicity of the drawing only four plates 8 are shown, each plate comprising a few corrugations. Convex sides of these corrugations project approximately transversely with respect to the concave sides of the adjacent corrugations. The convex projecting sides act as the separating members 10 which separate neighboring filter elements 7 from one another. In practice, use is made of, for example a large number of from, for example some tens to a few hundreds of parallel plates with from some tens to hundreds of corrugations each. The X-ray filter has, for example lateral dimensions (relative to the direction of the X-ray beam) of approximately 5 cm×5 cm. The capillary tubes have a length of approximately 1 cm. The corrugations in the embodiment shown are formed by acute folds with angles of approximately 120°, thus forming capillary tubes having a substantially hexagonal cross-section. The capillary tubes have a diameter of, for example 300 $\mu$m. Corrugated plates can also be used to form capillary tubes having a round or elliptical cross-section. Suitable materials for the plates are, for example plastic foils and glass foils having a thickness of between 2 $\mu$m and 20 $\mu$m; suitable results are obtained notably by means of a thin plastic or glass foil of a thickness of approximately 5 $\mu$m. Suitable plastic foils are notably polyethene, polyether sulphon or polyether terephtalate foils and the like.

One end of the capillary tubes communicates with the X-ray absorbing liquid 30 in a reservoir 31. A suitable X-ray absorbing liquid is, for example a solution of a lead salt such as lead perchlorate ($Pb(ClO_4)_2$) in demineralized water. Due to the capillary effect in the individual filter elements, X-ray absorbing liquid rises in the individual capillary tubes in dependence on the electric voltage applied to the relevant capillary tubes. The capillary effect is caused by adhesion between the X-ray absorbing liquid and the inner wall of the capillary tubes. This adhesion can be controlled on the basis of the electric voltage applied to the capillary tubes. If no or hardly any voltage difference exists between the wall of the relevant capillary tube and the X-ray absorbing liquid, the relevant capillary tube 7 is hydrophobic to the X-ray absorbing liquid. The degree of filling of such capillary tubes with the X-ray absorbing liquid can be controlled via the electric voltage applied to the relevant capillary tubes. It has been found that the adjustment of the X-ray filter can be changed within approximately 0.01 s.

Figure 3:
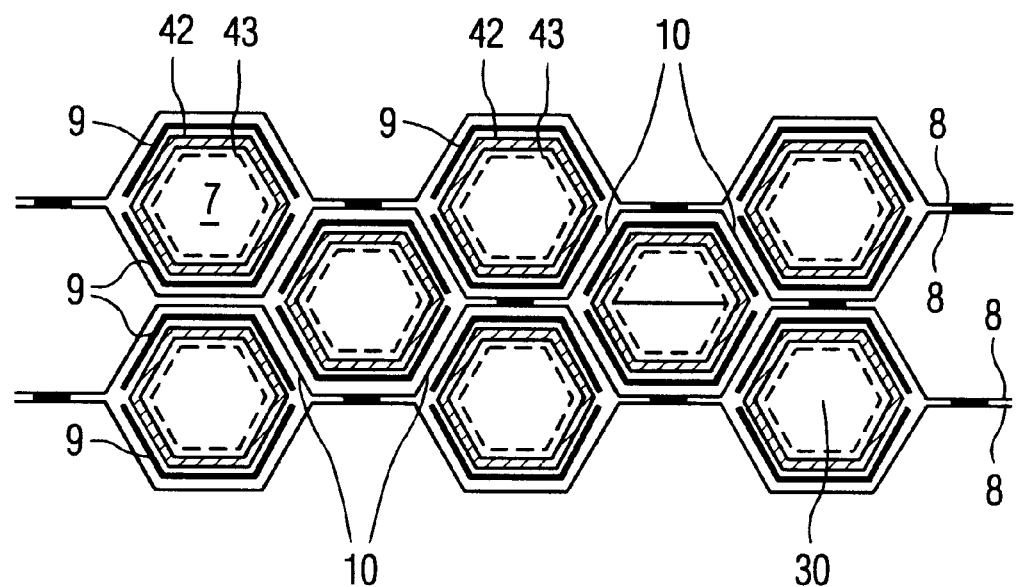
FIG. 3 is Plan view of the X-ray filter of FIG. 2.

FIG. 3 is a plan view of the X-ray filter used in an X-ray examination apparatus according to the invention.

Respective electrically conductive layers 9 are provided on the inner wall of the concave sides of the corrugations of the plates 8. An electrically conductive layer 9 is thus formed on the inner wall of the capillary tubes 7. It is ensured that electrically conductive layers 9 of different capillary tubes are suitably electrically insulated from one another. The electric voltages are applied to the electrically conductive layers of respective capillary tubes 7 via voltage leads 32. In order to form the electrically conductive layers, use is preferably made of a metal which can be suitably deposited by vapor deposition and has a low atomic number, and hence a low X-ray absorption. Notably aluminium, copper and chromium are suitable materials for forming the electrically conductive layer, because these materials can be readily provided on the plates by vapor deposition. Such an electrically conductive layer can also be formed by indium tin oxide (ITO) and silicon which could also be doped.

The electrically insulating layer 42 is provided on the electrically conductive layer 9. The electrically insulating layer is preferably a dielectric layer which electrically isolates the X-ray absorbing liquid from the electrically conductive layer 9 in order to maintain the electric potential difference between the electrically conductive layer 9 and the X-ray absorbing liquid 30. The relative dielectric constant of the dielectric layer is preferably comparatively large and the dielectric layer must be comparatively thin in order to ensure that the electric field caused by the charge on the electrically conductive layer suitably penetrates the dielectric layer. On the other hand, the electrical capacitance of the dielectric layer must be comparatively low so as to enable a fast variation of the charge on the electrically conductive layer. It has been found that parylene-n, having a relative dielectric constant of 2.65, and parylene-c, having a relative dielectric constant of 3.15, are suitable materials for forming the electrically insulating layer 42 with a thickness of between 2 $\mu$m and 10 $\mu$m. Moreover, parylene-c and notably parylene-n are suitably capable of withstanding electric breakdowns. Particularly parylene-n can be readily deposited by making the monomer polymerize on the surface of the electrically conductive layer. It is even possible to provide a parylene-n layer on the electrically conductive layer after corrugation of the plates and formation of the capillary tubes.

A hydrophobic coating layer 43 is provided on the electrically insulating layer 42. The coating layer 43 may be very thin; if necessary, the coating layer may be a molecular monolayer. Suitable hydrophobic properties are offered by coating layers whose surface is composed of $CH_3$, $CF_3$, $CH_2$ or $CF_2$ terminated silanes, siloxanes or other hydrocarbons. Furthermore, paraffin and polyfluoro hydrocarbons such as Teflon are also suitable hydrophobic coating layers. Such coating layers can be easily and nevertheless accurately deposited by vapor deposition from the gaseous phase.

The electrically conductive layer 9, the electrically insulating layer 42 and the hydrophobic coating layer 43 are provided on an as large as possible part of the inner side of the relevant capillary tube; it is thus achieved that only a very short period of time is required to fill the capillary tube with the X-ray absorbing liquid to a substantial extent.

Figure 4:
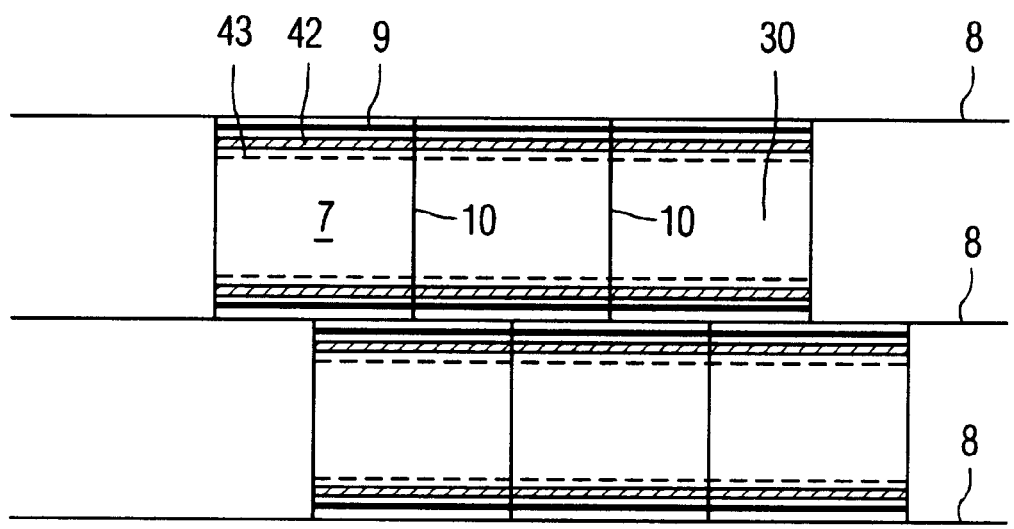
FIG. 4 is a plan view of another embodiment of an X-ray filter used in an X-ray examination apparatus according to the invention.

FIG. 4 is a plan view of a further embodiment of an X-ray filter used in an X-ray examination apparatus according to the invention. The substantially parallel plates 8 are provided with partitions 10 which act as separating members. Parts of the plates 8 between neighboring partitions 10 constitute capillary tubes 7. On parts of the plates between the partitions an electrically conductive layer is provided on the side facing the inner side of the capillary tubes; on said electrically conductive layer there is provided the dielectric layer which is covered by the hydrophobic coating layer. When the partitions are also covered with an electrically conductive layer on which an electrically conductive layer and a hydrophobic coating layer are provided, an as large as possible part of the inner side of the capillary tubes will be covered by said layers.

Separate voltage leads 32 are provided for individual plates 8. The electrically conductive parts are electrically coupled to the relevant voltage lead via respective switches 33. Notably $\alpha$-Si thin-film MOS transistors are suitable switches for controlling the X-ray filter. The voltage leads 32 are coupled to an electric voltage source 35 via a column driver 34. The column driver provides the distribution of desired electric voltages among the electrically conductive parts 9 of individual plates 8. Preferably, electric voltages are used in the range of from 30 V to 100 V; in that case switches in the form of α-thin-film transistors can be used.

Control lines 36 for control of the thin-film transistors 33 are provided per row of electrically conductive parts of individual plates 8, said control leads being electrically coupled to the respective gate contacts 37 of the thin-film transistors 33. Each of the thin-film transistors 33 is connected, by way of its source contact 38, to the relevant voltage lead 32 whereas its drain contact 39 is coupled to the respective electrically conductive track 9. The respective thin-film transistors 33 are closed, i.e. electrically turned on, by applying a control signal to the relevant control lead. The control signals are supplied by a row driver 40. By closing the relevant thin-film transistor 33 by means of a control signal and by applying at the same time an appropriate voltage via the corresponding control lead, the voltage on the relevant electrically conductive track is adjusted to the desired value. Consequently, in the vicinity of said electrically conductive track the hydrophobicity of the plate 8 is cancelled and the area in the vicinity of said electrically conductive track is filled with the X-ray absorbing liquid. The degree of filling is dependent on the applied electric voltage. The row driver 40, the column driver 34 and the electric voltage source 35 form part of the adjusting unit 50.

All references cited herein, as well as the priority document European Patent Application 97201544.0 filed May 23, 1997, are incorporated herein by reference in their entirety and for all purposes to the same extent as if each individual publication or patent or patent application was specifically and individually indicated to be incorporated by reference in its entirety for all purposes.

What is claimed is:

1. An X-ray examination apparatus comprising:

an X-ray source an X-ray detector and an X-ray filter which is arranged between the X-ray source and the X-ray detector, wherein the X-ray filter further comprises a plurality of adjacently situated plates arranged in a substantially parallel manner to form a plurality of filter elements in spaces between the plates, wherein the X-ray absorptivity of the filter elements can be adjusted by controlling a quantity of an X-ray absorbing liquid individually in each of the individual filter elements such that in the absence of the X-ray absorbing liquid the absorptivity of a filter element is negligibly small, and a reservoir for the X-ray absorbing liquid which communicates with each of the filter elements.

2. An X-ray examination apparatus as claimed in claim 1 wherein the plates are corrugated.

3. An X-ray examination apparatus as claimed in claim 2 wherein the corrugations of adjacently situated corrugated plates form separating members which constitute filter elements having an essentially hexagonal cross-section.

4. An X-ray examination apparatus as claimed in claim 1 further comprising a plurality of partitions which are arranged to project transversely from the plane of the plates, and wherein the partitions of adjacently situated plates form separating members which constitute filter elements.

5. An X-ray examination apparatus as claimed in claim 1, characterized in that adjacently situated plates are interconnected between neighboring filter elements.

6. An X-ray examination apparatus as claimed in claim 1 wherein the inner surface of the filter elements comprises an electrically conductive layer.

7. An X-ray examination apparatus as claimed in claim 2, characterized in that an electrically conductive layer is provided on a concave side of the relevant corrugation.

8. An X-ray examination apparatus as claimed in claim 7, characterized in that an electrically insulating layer is provided on the electrically conductive layer.

9. An X-ray examination apparatus as claimed in claim 7, characterized in that a hydrophobic coating layer is provided on the electrically conductive layer.

10. An X-ray examination apparatus as claimed in claim 8, characterized in that a hydrophobic coating layer is provided on the electrically insulating layer.

11. An X-ray examination apparatus as claimed in claim 2, characterized in that adjacently situated plates are interconnected between neighboring filter elements.

12. An X-ray examination apparatus as claimed in claim 4, characterized in that adjacently situated plates are interconnected between neighboring filter elements.

13. An X-ray examination apparatus as claimed in claim 2 wherein the inner surface of the filter elements comprises an electrically conductive layer.

14. An X-ray examination apparatus as claimed in claim 4 wherein the inner surface of the filter elements comprises an electrically conductive layer.

15. An X-ray examination apparatus as claimed in claim 13, characterized in that an electrically insulating layer is provided on the electrically conductive layer.

16. An X-ray examination apparatus as claimed in claim 14, characterized in that an electrically insulating layer is provided on the electrically conductive layer.

17. An X-ray examination apparatus as claimed in claim 13, characterized in that a hydrophobic coating layer is provided on the electrically conductive layer.

18. An X-ray examination apparatus as claimed in claim 14, characterized in that a hydrophobic coating layer is provided on the electrically conductive layer.

19. An X-ray examination apparatus as claimed in claim 15, characterized in that a hydrophobic coating layer is provided on the electrically insulating layer.

20. An X-ray examination apparatus as claimed in claim 16, characterized in that a hydrophobic coating layer is provided on the electrically insulating layer.

21. The apparatus of claim 1 wherein the plates comprise a plastic foil or a glass foil with a negligibly small X-ray absorptivity.

22. The apparatus of claim 1 wherein the plates are less than 20 micrometers in thickness.

* * * * *